(12) United States Patent
Cordeiro et al.

(10) Patent No.: US 8,802,877 B2
(45) Date of Patent: Aug. 12, 2014

(54) PROCESS FOR MODIFYING VEGETABLE OILS AND PRIMARY PLASTICIZER FOR VINYL POLYMERS

(75) Inventors: Milton Sobrosa Cordeiro, Mogi das Cruzes (BR); Sérgio Teixeira, Mogi das Cruzes (BR); Ariovaldo Fernandes Junior, Mogi das Cruzes (BR)

(73) Assignee: NPC Industrias Quimicas Ltda, Mogi das Cruzes - SP (BR)

( * ) Notice: Subject to any disclaimer, the term of this patent is extended or adjusted under 35 U.S.C. 154(b) by 253 days.

(21) Appl. No.: 13/516,410

(22) PCT Filed: Dec. 17, 2009

(86) PCT No.: PCT/BR2009/000428
§ 371 (c)(1),
(2), (4) Date: Jul. 31, 2012

(87) PCT Pub. No.: WO2011/072346
PCT Pub. Date: Jun. 23, 2011

(65) Prior Publication Data
US 2012/0289727 A1 Nov. 15, 2012

(51) Int. Cl.
*C11C 3/10* (2006.01)
(52) U.S. Cl.
USPC .......................... 554/169; 554/167; 554/168
(58) Field of Classification Search
USPC ......................................... 554/167, 168, 169
See application file for complete search history.

(56) References Cited

U.S. PATENT DOCUMENTS

| 2,559,177 A | 7/1951 | Terry et al. |
| 3,070,608 A | 12/1962 | Kuester et al. |
| 3,275,584 A | 9/1966 | Kraft et al. |
| 5,324,846 A | 6/1994 | Hirshman et al. |
| 2002/0099230 A1 | 7/2002 | Ramirez-de-Arellano-Aburto et al. |

FOREIGN PATENT DOCUMENTS

| AU | 778808 B2 | 12/2004 |
| GB | 934689 | 8/1963 |
| GB | 1341623 | 12/1973 |
| KR | 2005/068297 A | 9/2005 |
| WO | WO 00/73254 A1 | 12/2000 |
| WO | WO 2009/094310 A2 | 7/2009 |

OTHER PUBLICATIONS

Daniel Swern, "Plasticizers" The Journal of the American Oil Chemists' Society, vol. 31, Nov. 1954, pp. 574-578.

*Primary Examiner* — Deborah D Carr
(74) *Attorney, Agent, or Firm* — Fanelli Haag & Kilger PLLC

(57) ABSTRACT

The present invention refers to a process for modifying epoxidized or non-modified vegetable oils. More specifically, it refers to the process through which vegetable oils and alcohols are converted into fatty acid alkyl esters through transesterification. The present invention also refers to the products obtained through the process disclosed herein.

17 Claims, 2 Drawing Sheets

PROCESS FOR MODIFYING VEGETABLE OILS AND PRIMARY PLASTICIZER FOR VINYL POLYMERS

This application is a National Stage of PCT/BR2009/000428, filed Dec. 17, 2009, the disclosure of which is incorporated herein by reference in its entirety.

FIELD OF THE INVENTION

This invention refers to a process for modifying vegetable oils. More specifically, it refers to a process through which vegetable oils and alcohols are converted into epoxidized fatty acid alkyl esters. The present invention also refers to the products obtained through the process disclosed herein. Said products may be used as primary plasticizers for vinyl polymers, particularly for halogenated plastics, especially polyvinyl chloride (PVC).

BACKGROUND OF THE INVENTION

Polyvinyl chloride (PVC) is the best known and most widely used vinyl polymer. It is used mainly in two forms: (i) rigid PVC; and (ii) flexible PVC. The rigid form of PVC, known as non-plasticized PVC, is generally used to produce pipes, connections, profiles and frames, as well as applications where chemical resistance is necessary. The flexible form of PVC, also known as plasticized PVC, is used in films, blankets, electrical insulators, flooring, toys, wallpapers, synthetic leather used for clothes, footwear and coatings, among many other end products.

Malleability and flexibility are physical characteristics that may be modulated by formulating a specific polymeric resin with one or more materials that can serve as plasticizers. In a broad definition, a plasticizer may be understood as a substance with a high boiling point that when included in a polymeric matrix confers and preserves the flexibility of the material. The plasticizer become an integral part of the polymer and must provide the benefits of plastification throughout the entire useful life of the product.

One of the most relevant characteristics of a plasticizer is its compatibility with the polymeric resin. The primary plasticizers are highly compatible with the polymer and may be included to it in large amounts, with no exudation. In addition to the above-mentioned malleability and flexibility, these additives may provide better coloring, easier processing and broader range of applications. The primary PVC plasticizers are generally petroleum derivatives, among which are phthalates, adipates, trimellitates, benzoates, azelates and polymers.

The secondary plasticizers are moderately compatible with the polymeric resin and are generally used together with a primary plasticizer in order to reduce costs or to obtain specific properties. The chlorinated paraffins (PCs) are the most common examples of secondary plasticizers for PVC resins, widely used as they present low flammability and low cost. Other examples of secondary plasticizers are the poly-alpha methyl styrene derivatives and vegetable oils derivatives.

Some concerns regarding the toxicity and performance of some primary plasticizers traditionally used by the halogenated plastics industry, and the constant need to improve PVC formulations, have driven the search for alternatives. In the recent years, much interest has been focused on plasticizers that may be obtained from precursors generated through microbiological processes or from renewable sources, such as citrates and modified vegetable oils.

For example, epoxidized vegetable oils have been used in small proportions as secondary plasticizers and thermo-costabilizers in the production of flexible, semi-rigid and rigid PVCs. However, the use of epoxidized triglycerides as primary plasticizers results in exudation due to the limited compatibility with the polymeric matrix. In order to enhance the compatibility of the vegetable oils with PVC, some modifications, in addition to epoxidation, were proposed: esterified (GB 1020866), interesterified and acetylated derivatives were suggested as primary plasticizers for PVC resins. Among the products generated by these processes are the acetylated/epoxidized mono- and di-glycerides and epoxidized fatty acid alkyl esters.

The methods for production of epoxidized fatty acid alkyl esters generally involve two steps. The first step is to transform fatty acids or a vegetable oil into fatty acid alkyl esters. This transformation may be conducted through esterification (when the precursors are fatty acids) or transesterification (when the precursors are vegetable oils or fatty esters with short alkyl chain).

The esterification is a reaction between carboxylic acids and alcohols that generates esters and water as products. As this is a balance reaction, the water produced is generally removed from the system in order to favor the formation of the ester. Fatty acids esterification is normally conducted in the presence of an acid catalyst (for example, $H_3PO_4$, $H_2SO_4$, $CH_3C_6H_4SO_3H$, $CH_3SO_3H$, among others), at temperatures higher than 120° C. Titanates may also be used as catalysts in esterification, however higher temperatures are required (>200° C.) in order to the reaction be effective. When alcohols with high boiling points are used, temperatures of over 230° C. allow esterification to be achieved with no catalyst, however, the end product is dark and requires treatment to improve its coloring.

The transesterification is a process through which an ester is reacted with an alcohol in order to form a new ester and an alcohol resulted from the initial ester. This reaction may be used when the precursors are low acidity vegetable oils or fatty acid esters with short alkyl chain—typically methyl or ethyl esters. The transesterification is normally conducted at moderate temperatures (below 130° C.), requires anhydrous conditions and may be catalyzed by an acid or a base, generally in the homogenous phase. The acid catalyst may be $H_2SO_4$, HCl, $H_3PO_4$, $CH_3C_6H_4SO_3H$, among others. The basic catalysts most commonly used for transesterification are alkaline metals hydroxides or alcoxides, such as NaOH, KOH, LiOH, $NaOCH_3$ and $KOCH_2CH_3$.

The other required step to obtain epoxidized fatty acid alkyl esters is epoxidation. In the epoxidation the double bounds presented in the different fatty acid alkyl ester chains (products obtained through esterification or transesterification) are converted into epoxide groups (or oxirane). This reaction must take place after an esterification step, or may be conducted before or after a base-catalyzed transesterification step.

The epoxide groups may be incorporated by using any appropriate technique. The most widely used procedure is the reaction with a percarboxylic acid, pre-formed or generated in situ through hydrogen peroxide and an aliphatic organic acid, usually formic acid or acetic acid. Said epoxidation techniques are well known in the science. In addition to making the products compatible with the polymeric resin, the presence of oxirane rings in the fatty acid esters chains significantly contributes to the photo-thermal stability of the end material.

As mentioned above, the esterification of carboxylic acids is usually catalyzed by acids and the transesterification may be catalyzed by bases or by acids. For example, BR 0602925-6 describes a process for the preparation of fatty acid esters and their subsequent epoxidation in order to produce plasticizers and the resulting product. The invention describes the preparation of methyl or ethyl esters through transesterification catalyzed by methoxide or ethoxide of an alkaline metal. These esters with short alkyl chain were used as precursors in order to produce other fatty acid alkyl esters from polyols and alcohols with medium and long chains, in transesterification reactions catalyzed by acids, preferably methane sulfonic acid, with the catalyst not varying as a function of the alcohol used. For alcohols with high boiling points, titanates were the preferred catalysts. The obtained esters were subsequently epoxidized with peracid.

In cases where the catalyst used to obtain the alkyl esters is an acid, normally it is not possible to directly convert the raw materials containing epoxide groups, as is the case of epoxidized fatty acids or epoxidized vegetable oils. In the presence of an alcohol and an acid catalyst, the epoxide groups present in these precursors are partially or fully converted into hydroxy ethers. Bearing in mind that the presence of the epoxide group is fundamental for the good performance of the plasticizer, the product presents a reduction in its functionality. In these cases, in order to offset this drawback, the epoxidation stage must always be conducted after the esterification step (or transesterification catalyzed by an acid).

The epoxidized vegetable oils, as well as epoxidized fatty acid methyl or ethyl esters, may be directly converted into epoxidized alkyl esters by base-catalyzed transesterification. In this case, there is not the drawback of parallel reactions between the epoxide groups and the alcohol used in the reaction. However, if the base catalyst is a hydroxide (LiOH, NaOH, KOH, etc.), its reaction with the alcohol forms water. Even if present in small quantities in the reaction mixture, the water results in the formation of soap, occurring reduction in the alkalinity of the catalyst and greater difficulty during the subsequent purification step, due to formation of emulsions. Another problem related to the hydroxides is that when alcohols with medium or long chains are used in transesterification catalyzed by these bases, a good conversion is achieved only with two or more transesterification stages, required to ensure satisfactory conversion of the vegetable oil into fatty acid alkyl esters.

On the other hand, alkaline metal alcoxides, such as sodium methoxide or ethoxide, are effective catalysts and do not form water in the reaction mixture during vegetable oils transesterification. Generally, alcoxides are commercially available in the form of solutions; for example, sodium methoxide is sold as a 30% in methanol solution. For transesterification involving alcohols with medium and long chain, the use of these catalysts in an alcohol solution results in an end product with appreciable quantities of fatty esters with short alkyl chain in its composition.

Epoxidized fatty acids methyl or ethyl esters may satisfactorily serve as PVC plasticizers in less sensitive applications, such as the production of certain calandered and extruded materials. However, the use of these epoxidized fats esters with short alkyl chain or plasticizers containing these compounds may cause problems in some situations. The relatively low molar mass of these compounds may restrict their application, especially when the PVC compounds and plastisols are processed at temperatures above 190° C. Under such conditions, intensive volatization during the processing and exudation in the obtained polymeric materials are noted.

The use of pure alcoxides is one way of reducing the formation of esters with short chain in transesterification reactions that involve alcohols with medium or long chain. However, as a solid, sodium methoxide is extremely poisonous, causing damage to mucous tissues and to the respiratory tract, it is thus avoided as it is difficult to handle. Sodium ethoxide, another alcoxide available in solution, is extremely hygroscopic in its solid form. On the other hand, potassium tert-butoxide is an alcoxide sold as a pure solid and with good stability, nevertheless its price is relatively high making a significant contribution to large scale process costs, as it is the case of PVC plasticizers production.

In their elementary form, alkaline metals are highly reactive and require special care when being handled and used. They react with water, forming hydrogen and hydroxide, and there is the possibility of explosion, depending on the quantity involved. Although knowing that alkaline metals may be used in transesterification processes, the teachings of the state of the art do not suggest said use for producing PVC plasticizers from vegetable oils. This possibly occurs due to the difficulties and risks involved in the use of alkaline metals in their elementary forms, in addition to a false impression of high costs.

The patent application US 20090149586 describes a process for the synthesis of primary plasticizers for PVC comprised by epoxidized fatty acids ethyl or isoamyl esters and PVC compositions prepared with said esters. The catalyst used in the process was sodium hydroxide (3.8% in relation to the soya oil mass) using molar ratios of refined soya oil to alcohol of 1:10 to 1:30, which are far higher than the traditional ratio of 1:6 used in the transesterification of refined oils. After transesterification, the obtained alkyl esters were epoxidized with percarboxylic acid generated in situ. This document neither describes nor suggests the use of alkaline metal as a catalyst precursor. Moreover, attempts to reproduce the teachings set forth in this document indicated the need for at least two transesterification stages in order to obtain an end product with acceptable purity.

There are also other drawbacks in processes for modifying vegetable oils known in the state of the art, which are related to the fatty acid esters purification. When the process involves the transesterification of a vegetable oil, glycerin separation may require prolonged periods, the washing of the product may demand large amounts of water, and the removal of excess alcohol, if it presents a high boiling point, normally requires high vacuum, which requires heavy investments.

It is an objective of the present invention the use of alcohols with medium and long chain in transesterification and obtaining epoxidized fatty acid esters with long and medium alkyl chains, free from epoxidized methyl and ethyl esters.

It is also an objective of the present invention the use of alkaline metal to produce an alcohol derivative alcoxide catalyst used as a transesterification reagent.

Another objective of the present invention is to provide a new and improved process for modifying vegetable oil in order to obtain products that serve as high grade primary plasticizers in vinyl polymer formulations that may be used in high concentrations, providing to the polymer the desired qualitative aspects, maintaining the fundamental qualities of the end material.

Further characteristics, aspects and advantages of the present invention will become more clearly apparent through reading the following descriptions.

DESCRIPTION OF THE INVENTION

The present invention refers to a process for modifying vegetable oils in order to obtain primary plasticizers for vinyl polymers.

The present invention also refers to the products obtained through the process described herein, which are epoxidized fatty acid alkyl esters. Said products may be used as primary plasticizers for vinyl polymers, presenting performances identical or superior to those of traditional plasticizers.

The process for modifying vegetable oil of the present invention comprises, more specifically, the transesterification of at least one vegetable oil with at least one monohydric alcohol, with a chain size longer than 3 carbon atoms, and/or with at least one polyhydric alcohol of any type, being catalyzed by an alcoxide generated by the reaction of the said alcohol (or alcohols) with an alkaline metal.

The process of the present invention comprises, preferably, a single transesterification stage. However, two or more transesterification stages may be carried out.

The process of the present invention may be conducted with epoxidized vegetable oils as well as with non-modified vegetable oils.

Within the context of the present invention, a fatty acid ester with short alkyl chain is understood as presenting up to 3 carbon atoms in its alkyl portion; medium chains are those presenting 4 to 7 carbon atoms in the alkyl portion; with long chain are those presenting 8 or more carbon atoms in the alkyl portion. This nomenclature extends to the alcohols used in the preparations of these esters, in other words, alcohols with short chain contain up to 3 carbon atoms; alcohols with medium chain are those with 4 to 7 carbon atoms, and alcohols with long chain are those with 8 or more carbon atoms. The polyols that may be used in the process are not encompassed by these definitions.

In a first aspect of the present invention, at least one epoxidized vegetable oil is reacted with at least one monohydric alcohol, with a chain size of more than 3 carbon atoms, and/or with at least a polyhydric alcohol of any type, with this transformation being catalyzed by an alcoxide generated by the reaction of the said alcohol (or alcohols) with an alkaline metal. Under these circumstances, the primary plasticizer derived from vegetable oils is obtained in a single step, in a simple manner and with a high purity level.

In a second aspect of the present invention, the precursor is a non-modified vegetable oil. At least one oil non-modified is reacted with at least one monohydric alcohol, with a chain size longer than 3 carbon atoms, and/or with at least one polyhydric alcohol of any type, with this transformation being catalyzed by an alcoxide generated by the reaction of the said alcohol (or alcohols) with an alkaline metal. This reaction produces fatty acid alkyl esters that, in a second step, must be epoxidized in order to obtain the primary plasticizers.

Examples of epoxidized vegetable oils available on the market are Drapex 6,8, Vikoflex 7170, Vikoflex 7190, Soyflex 6330, etc.

Non-modified vegetable oils useful as precursors for the present process are those presenting high unsaturated fatty acid contents in their composition (more than 80% of unsaturated fatty acids), preferably oleic, linoleic and linolenic acids. Examples of suitable non-modified vegetable oils include soya, sunflower, maize, flaxseed, rapeseed, rubbertree seed or peanut oils, among other vegetable oils with more than 80% of unsaturated fatty acids in their composition. Blends of these vegetable oils are also encompassed by this application.

Examples of monohydric alcohols useful in the present invention are n-butanol, isobutanol, sec-butanol, tert-butanol, n-pentanol, sec-pentanol, isopentanol, hexanol, cyclohexanol, 1-octanol, 2-ethyl-hexanol, isononanol, isodecanol, tridecanol, fatty alcohols, among others, whose chain size is longer than 3 carbon atoms, preferably from 4 to 16 carbon atoms. Polyhydric alcohols (polyols) useful in the present invention are ethylene glycol, diethylene glycol, triethylene glycol, propylene glycol, dipropylene glycol, glycerol, neopentyl glycol, pentaerythritol, among other alcohols with more than one hydroxyl, preferably from 2 to 4 hydroxyls, with no restriction on the size of the carbon chain. Said alcohols may be used alone or in combination.

Any alkaline metal may be used in the process of the present invention. Preferably, metallic lithium, sodium or potassium are used, with metallic sodium being the most preferred.

The production of the catalyst through the reaction between an alkaline metal and alcohols with medium and long chain sizes allowed, in a surprisingly way, solving several of the problems mentioned in the background of the invention. The alkaline metal may be reacted with alcohols with medium or long chain during moderate periods (less than 2 hours), obtaining exclusive alcoxides from the alcohols used. These alcoxides present high efficiency as transesterification catalysts. The production of the catalyst in this manner is a comparative advantage of the present invention, and the application of the method was possible even using alcohols with chain size up to 16 carbon atoms. No process known in the state of the art involving transesterification, has used this methodology to produce epoxidized fatty acid esters with medium or long alkyl chains.

Tests conducted with alcohols containing up to 16 carbon atoms showed that, in addition to generating the alcoxide that serves as an efficient transesterification catalyst, the alkaline metal also reacts with the water that may be present in the alcohol, reducing the risk of formation of soap and emulsion.

The process of the present invention uses an alkaline metal as a precursor for a catalyst, generating a superior quality product, in contrast to the processes using alcoxides in solution available on the market. Even with a single transesterification stage, the epoxidized fatty acid alkyl esters are produced with high purity levels, excellent yield and without the formation of undesirably by-products, in addition to presenting excellent performance in application tests.

The quantity of alkaline metal for the preparation of the alcoxide varies, depending on the alcohol used in the process, ranging from 0.03 to 3.0% of the total reaction mass, preferably 0.06 to 2.5%. The reaction time of the alkaline metal with the alcohol may widely vary, ranging from 5 minutes to 2 hours, depending on the metal, the temperature and the type and quantity of alcohol.

The quantity of alcohol used may vary from the stoichiometric up to 300% above this amount, in relation to the vegetable oil, most frequently in the range of 20 to 200% of excess.

The reaction of the alkaline metal with the alcohol preferably occurs before the transesterification. In this case, once the reaction between the alkaline metal and the alcohol has ended, the pre-heated vegetable oil (preferably up to the temperature at which the transesterification will occur) is added to the produced alcoxide. Alternatively, but less recommended, the alkaline metal may be added to the reaction mixture (oil and alcohol). As set forth in the present invention, when using an epoxidized vegetable oil, as well as when using an non-modified vegetable oil, the preparation of the alcoxide and the transesterification take place under inert atmosphere (nitrogen or argon) or under low pressure (>600 mmHg).

The transesterification temperature may vary from 25 to 220° C. depending on the type of alcohol used, preferably from 50 to 160° C.

The time needed for the transesterification may vary from 10 to 300 minutes, depending on the type of oil and alcohol used, preferably from 20 to 240 minutes.

At the end of the transesterification reaction a purification step occurs through which the formed glycerin is decanted and separated. The reaction mixture is then neutralized with acid, washed and stripped (alcohol removal process), with steam and under a discreet vacuum (up to about 600 mmHg), at temperatures varying from 120 to 220° C., depending on the type of alcohol which is retrieved and re-used in subsequent production. After the alcohol removal process, the product is filtered. When the precursor is an epoxidized vegetable oil, the primary plasticizer derived from vegetable oils is ready.

According to the present process, the purification of the products obtained through the transesterification is quite simple.

Depending on the types and quantities of alcohol and vegetable oil used, triglycerides and/or partial glycerides may be present in the end product. Typically, these glycerides represent less than 4% of the total mass of the products, preferably less than 3%, with these compounds in these quantities causing no problems in the application of the plasticizers.

As set forth above, in order to prepare the products from alkyl esters obtained from vegetable oils with no prior structural modification (non-epoxidized), an epoxidation step is required. This procedure is conducted with performic acid, generated in situ by the reaction between hydrogen peroxide and formic acid. The hydrogen peroxide employed in this stage may be in the form of an aqueous solution at concentrations between 30 and 70% (m/m), preferably at concentrations between 40 and 70%. An acid catalyst ($H_2SO_4$, $H_3PO_4$ or a suitable acid resin such as Amberlite IR-120H) might or might not be used in this process. At the end of the reaction, the epoxidized esters are washed with water and diluted alkali in order to remove the acid reagent. After drying and filtration, the product is finished, as shown in FIG. 2.

No significant differences were noted in the composition of the products obtained from previously epoxidized substrates or substrates that were transesterified and epoxidized.

Due to its low solubility in the formed esters, the glycerin generated during transesterification begins to decant during the reaction, and is separated very easily. This allows the reaction mixture to be washed with small volumes of water (20 to 30% of the total reaction mass). As set forth above, the process of eliminating the excess of alcohol may be conducted with steam and a discreet vacuum (up to about 600 mmHg), at temperatures between 120 and 220° C., not being required the use of high vacuums, independently of the adopted route (epoxidation followed by transesterification or transesterification followed by epoxidation).

The alkaline transesterification and the purification process of the epoxidized fatty esters, as set forth in the present invention, keep the oxirane rings intact. The differences noted in the epoxy indexes of the precursors and the products obtained from different alcohols are due, basically, to differences in the molar masses of the alkyl fragments used in the synthesis of the epoxidized fatty esters.

The preparation of primary plasticizers derivative from vegetable oils and their properties in PVC formulations are illustrated in the following examples, although not being endowed with any limiting characteristics.

BRIEF DESCRIPTION OF THE FIGURES

The FIG. 1 illustrates a diagram of the process of producing fatty acid alkyl esters from epoxidized vegetable oils as described in Examples 1 and 2: (1) represents the reactor for the preparation of the catalyst; (2) represents the recycled alcohol storage tank; (3) represents the transesterification reactor; (4) represents a recipient used for the glycerin separation, neutralization and washing of the reaction mixture; (5) represents the stripper in which the alcohol is removed from the product; (6) represents an alcohol dehydration column; (7) represents a press filter; (8) represents the holding tank; and (9) represents the product storage tank.

The FIG. 2 illustrates a diagram of the process of epoxidation of fatty acid alkyl ester, as described in Example 3: (10) represents the peroxide dosing tank; (11) represents the formic acid dosing tank; (12) represents the epoxidation reactor; (13) represents the recipient used for neutralization, washing and drying of the epoxidized product; (14) represents a press filter; (15) represents the holding tank; (16) represents the product storage tank; and (17) represents the condensates recipient tank.

EXAMPLES

Example 1

Figure 1:
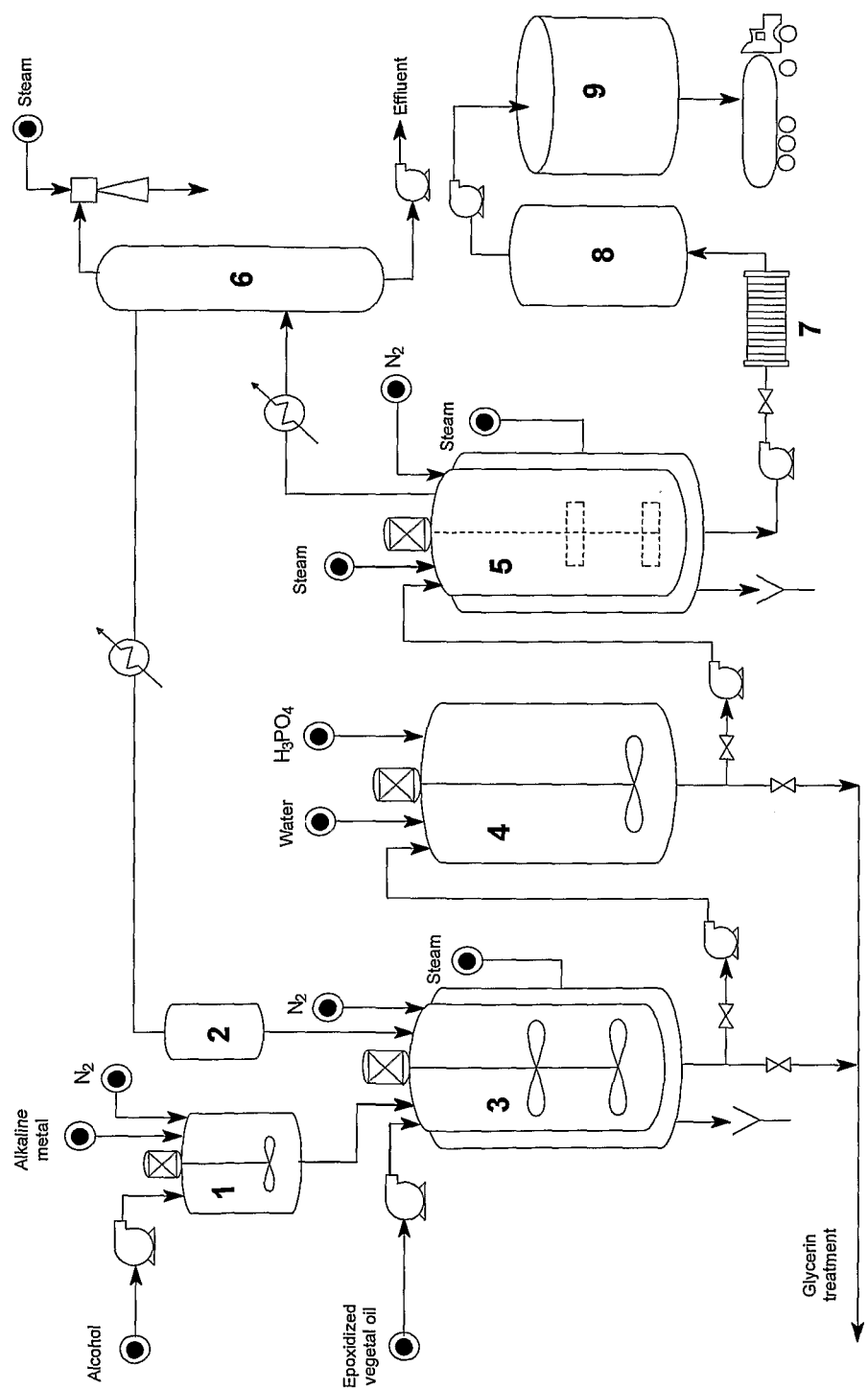
Figure 2:
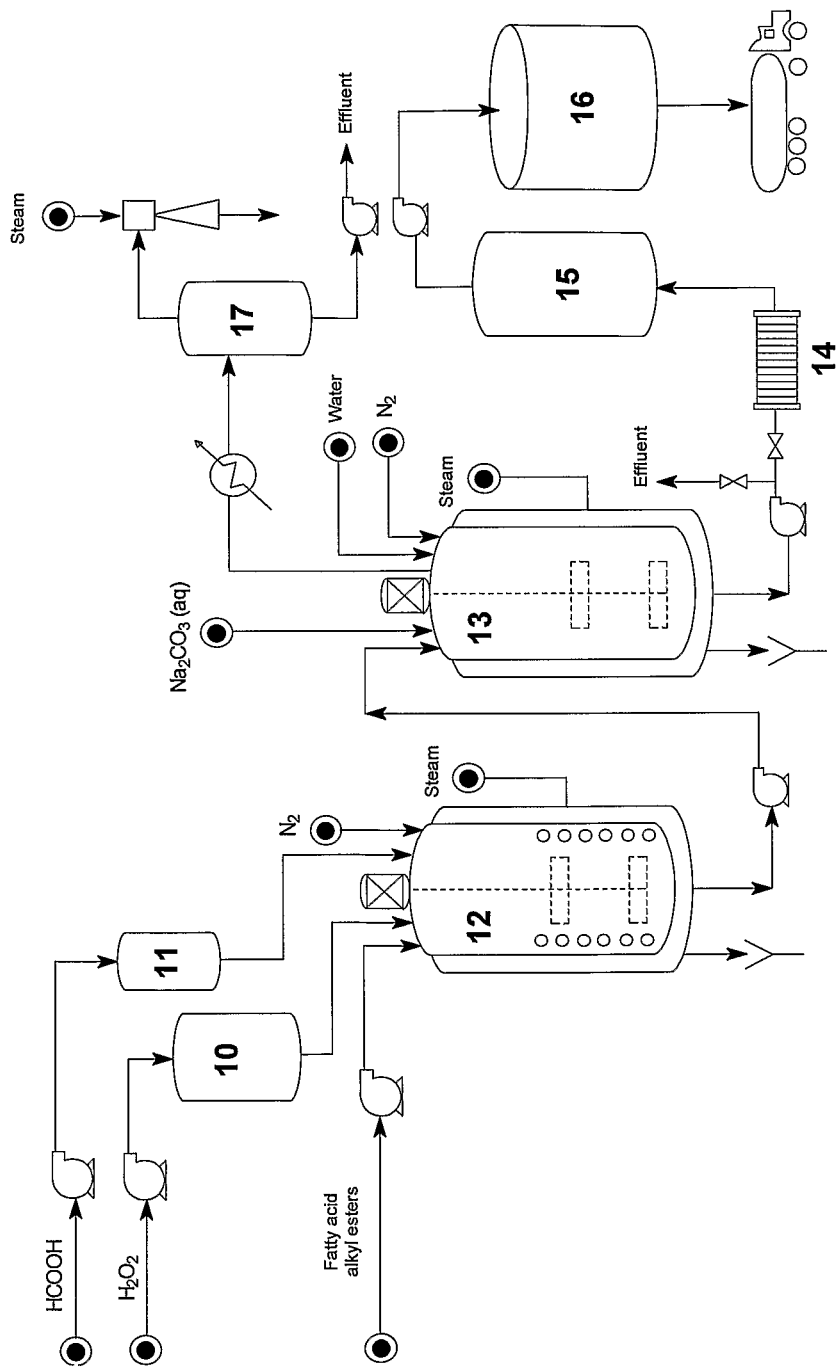

Approximately 55 kg of isopentyl alcohol were transferred to the catalyst preparation tank. After the system was inerted with nitrogen, 0.7 kg of sodium were added to the alcohol. After the reaction was completed, the alcohol containing the catalyst was transferred to the reactor, previously loaded with 100 kg of epoxidized soya oil (Drapex 6.8; epoxy index=6.7%) at a temperature of 70° C. Agitated at 200 rpm, the reaction was maintained for 2.5 hours at 75° C. After this period, the agitation was interrupted and the system was left in repose for 30 minutes. Most of the glycerin generated in the reaction was then drained off and the reaction mixture was transferred to a decantation tank. Water (around 20 L) and phosphoric acid (in an amount sufficient for neutralization) were added and the mixture was agitated for 15 minutes. Having been left at rest for one hour, the water containing salts and the rest of the glycerin was drained off. The mixture containing the product and alcohol was transferred to a stripper, which was operated under a vacuum of 600 mmHg at 150° C., using steam to draw off the alcohol. The separated alcohol was dehydrated in a distillation column and channeled for re-use. Finally, the product was filtered in a press filter, yielding 110 kg of fatty acid isopenthyl esters. This product presented the following characteristics: acidity index=0.81 mg KOH/g; epoxy index=5.6%; density [20° C.]=0.934 g·cm$^{-3}$; color APHA=350; viscosity [20° C.]=27 cP.

Example 2

About 700 g of isononanol were reacted with 4.8 g of metallic sodium in a nitrogen atmosphere. The alcoxide obtained in this manner was reacted with 800 g of epoxidized soya oil (Drapex 6.8; epoxy index=6.7%) during 2.5 hours at 90° C. The neutralization, washing and stripping took place as described in Example 1. After filtering, approximately 970 g of epoxidized fatty acid isononyl esters were isolated, with the following characteristics: acidity index=0.95 mg KOH/g; epoxy index=4.8%; density [20° C.]=0.923 g·cm$^{-3}$; color APHA=400; viscosity [20° C.]=47 cP.

Example 3

In a nitrogen atmosphere, approximately 800 g of isononanol were reacted with 4.9 g of metallic sodium. After the complete reaction of the sodium with the alcohol, 800 g of refined flaxseed oil were added to the generated alcoxide, and the reaction was maintained for 2.5 hours at 85° C. After the separation of the glycerin, the reaction mixture was neutralized, washed and stripped. After filtering, approximately 1000 g of isononyl fatty esters were isolated. About 500 g of this product were then expoxidized with performic acid generated in situ, in compliance with molar ratios double bounds: formic acid:hydrogen peroxide at 1:0.65:2. The epoxidation has continued for 5 hours at 70° C. and, after washing the reaction mixture with diluted alkali, followed by drying and filtering, approximately 520 g of epoxidized fatty acid isononyl esters were obtained, with the following characteristics: acidity index=0.25 mg KOH/g; epoxy index=6.15%; density [20° C.]=0.942 g·cm$^{-3}$; color APHA=60; viscosity [20° C.]=51 cP.

Examples of Applications

PVC formulations were prepared in compliance with the values described in Table 1. The quantity of each component in the formulation is expressed in "pcr"—parts per hundred parts of resin—an indication of quantity by mass of a specific component in relation to hundred PVC resin mass units. The products obtained in Examples 1, 2 and 3 were used as primary plasticizers, and were compared with the following petrochemical plasticizers DEHP (di-2-ethylhexyl phthalate) and DINP (di-isononyl phthalate).

TABLE 1

| Component | Quantity (pcr) |
| --- | --- |
| PVC Resin[1] | 100.0 |
| Plasticizer | 60.0 |
| Stabilizer[2] | 3.0 |
| Lubricant[3] | 0.3 |

[1]Solvin 265 PY: obtained through polymerization in suspension, Solvay Indupa do Brasil S/A.
[2]Markstab IBZ-580: Ba/Zn-based concentrated liquid stabilizer, Inbra Indústrias Quimicas Ltda.
[3]Stearic acid, Indústria Agro-Quimica Braido Ltda.

The ingredients were processed for 5 minutes in a laboratory calander (Mecanoplast C 400), with rollers heated at 160° C. and adjusted to produce sheets with a thickness of 0.5 mm. The plasticized PVC obtained through the calander was then rolled and pressed in molds (200° C.; 110 bar; 200 seconds) in order to produce sheets with a uniform thickness. The sheets obtained in this manner were cut into test bodies that were used to determine their physical properties through conventional test methods (ASTM D 638-08, D 4703-07, D 792-08, D 2115-04 and D 2240-05 Standards). The properties of the plasticized PVC resins are described in Table 2.

TABLE 2

| Property | DEHP | DINP | Example 1 | Example 2 | Example 3 |
| --- | --- | --- | --- | --- | --- |
| Shore A hardness - immediate | 76.2 | 80.5 | 72.6 | 80.1 | 74.6 |
| Shore A hardness - after 15 s | 70.3 | 73.1 | 66.7 | 70.5 | 68.0 |
| Specific weight (g · cm$^{-3}$) | 1.211 | 1.206 | 1.187 | 1.178 | 1.195 |
| Mass loss: 24 h @ 105° C. (%) | 0.38 | 0.37 | 1.15 | 0.36 | 0.61 |
| Mass loss: 168 h @ 105° C. (%) | 4.82 | 4.61 | 4.69 | 1.61 | 0.62 |
| Mass loss: extraction with heptanes for 24 h (%) | 7.42 | 6.04 | 1.49 | 5.73 | 1.09 |
| Mass loss: extraction with heptanes for 168 h (%) | 8.94 | 9.83 | 2.48 | 6.48 | 1.49 |
| Breaking force (N) | 171 | 178 | 170 | 186 | 176 |
| Tension (MPa) | 17.0 | 17.0 | 16.5 | 16.5 | 15.8 |
| Deformation (%) | 520 | 533 | 550 | 540 | 500 |

The presented data show that the plasticizers derived from vegetable oil of the present invention can serve as primary PVC plasticizers, and that excellent physical characteristics may be obtained. In addition to not presenting exudation signs, the test bodies prepared with the alternative plasticizers performed just as well as those prepared with traditional petrochemical plasticizers. In some critical trials, such as the extraction tests, the alternative plasticizers have superior performance comparing to phthalates.

Table 3 presents the components used to prepare the plastisols in order to obtain the flattened test bodies. The viscosity results for the prepared plastisols are described in Table 4.

TABLE 3

| Component | Quantity (pcr) |
| --- | --- |
| PVC Resin[1] | 100.0 |
| Plasticizer | 60.0 |
| Kicker[2] | 1.5 |
| CS-4M[3] | 2.5 |

[1]Solvin 367 NK: obtained through polymerization in microemulsion, Solvay Indupa do Brasil S/A.
[2]Plastabil K-219: Zn/K-based expansion auxiliary, Inbra Indústrias Quimicas Ltda.
[3]Planagen CS-4M: azodicarbonamide, Inbra Indústrias Quimicas Ltda.

The plastisols obtained from the product in Example 2 and with DINP were spread on paper in order to obtain films with approximately 1.0 mm thick, which were then heated in an LTE-S hot box (Mathis AG) under different time and temperature conditions. Results of thickness and gram weight of the prepared films are illustrated in Table 5.

TABLE 4

| | Viscosity (cP) | | |
| --- | --- | --- | --- |
| | After preparation | After 24 hours | After 48 hours |
| Plastisol (DINP) | 3100 | 4200 | 4400 |
| Plastisol (Ex. 2) | 5500 | 5600 | 6100 |

TABLE 5

| | Expansion Temperature (° C.) | Expansion Time (s) | Film Thickness (mm) | Gram Weight (g/m$^2$) | Exudation |
| --- | --- | --- | --- | --- | --- |
| Plastisol DINP | 190 | 90 | 2,201 | 590 | No |
| | 200 | 60 | 2,206 | 597 | No |
| Plastisol Ex. 2 | 190 | 90 | 2,411 | 598 | No |
| | 200 | 60 | 2,290 | 594 | No |

The results obtained for flattened PVC test bodies prepared with DINP and with the alternative plasticizer of Example 2 are quite close. Although the relative increase in the viscosity of the plastisol is higher over time, the product described in Example 2 allows the de-aeration just as quickly as the plastisol obtained with DINP. No indication of exudation was observed in the plastisol obtained with the product of the Example 2 after six months of observation. These characteristics confirm the feasibility of fully replacing phthalates by plasticizers of vegetable origin, as proposed in this invention, in plastisol formulation.

As clearly understood by people skilled in the art, many modifications and variations on the present invention are possible in the light of the explanations presented above without extending beyond the scope of its protection, as demarcated by the set of claims.

The invention claimed is:

1. PROCESS FOR MODIFYING VEGETABLE OIL, characterized by the fact that it comprises the following steps:
   a) react at least one monohydric alcohol, with a chain size of more than 3 carbon atoms, and/or at least one polyhydric alcohol of any type with an alkaline metal to generate an alcoxide; and
   b) perform the transesterification of at least one epoxidized vegetable oil with said alcohol (or alcohols), using the alcoxide generated in step a) as catalyst.

2. PROCESS FOR MODIFYING VEGETABLE OIL, characterized by the fact that it comprises the following steps:
   a) react at least one polyhydric alcohol of any type with an alkaline metal to generate an alcoxide; and
   b) perform the transesterification of at least one non-modified vegetable oil with said alcohol (or alcohols), using the alcoxide generated in step a) as catalyst.

3. PROCESS, according to claim 1, characterized by the fact that the epoxidized vegetable oil is selected from epoxidized soybean oil, epoxidized linseed oil, and blends thereof.

4. PROCESS, according to claim 2, characterized by the fact that an additional epoxidation stage must be conducted after the transesterification step.

5. PROCESS, according to claim 4, characterized by the fact that the non-modified vegetable oil includes more than 80% of unsaturated fatty acids in its composition.

6. PROCESS, according to claim 1, characterized by the fact that the monohydric alcohols are selected from n-butanol, isobutanol, sec-butanol, tert-butanol, n-pentanol, sec-pentanol, isopentanol, hexanol, cyclohexanol, 1-octanol, 2-ethyl-hexanol, isononanol, isodecanol, tridecanol, fatty alcohols or blends thereof.

7. PROCESS, according to one of claim 1 or 2, characterized by the fact that the polyhydric alcohols are selected from alcohols with more than one hydroxyl, preferably 2 to 4 hydroxyls.

8. PROCESS, according to one of claim 1 or 2, characterized by the fact that the reaction of the alkaline metal with the alcohol in order to produce alcoxide occurs before the transesterification, wherein once the alcoxide is generated, the vegetable oil pre-heated preferably up to the temperature at which the transesterification stage will occurs, varying from 25 to 220° C., will be added to the produced alcoxide.

9. PROCESS, according to one of claim 1 or 2, characterized by the fact that the alkaline metal is directly added to the vegetable oil and alcohol mixture.

10. PROCESS, according to claim 8, characterized by the fact that the quantity of alkaline metal used in the preparation of the alcoxide varies from 0.03 to 3.0% of the total reaction mass.

11. PROCESS, according to claim 8, characterized by the fact that the preparation of the alcoxide and the transesterification are conducted in an inert atmosphere (nitrogen or argon) or under reduced pressure (>600 mmHg).

12. PROCESS, according to claim 4, characterized by the fact that the epoxidation is conducted with performic acid generated in situ by the reaction between hydrogen peroxide and formic acid.

13. PROCESS, according to claim 12, characterized by the fact that the hydrogen peroxide is in the form of an aqueous solution at concentrations between 30 and 70% (m/m).

14. PROCESS, according to claim 1 or claim 2, characterized by the fact that it encompasses a purification step in which, at the end of the transesterification reaction, the formed glycerin is decanted and separated, after which the reaction mixture is neutralized with acid, washed and stripped (alcohol removal process) with steam and under a discreet vacuum (up to about 600 mmHg), at temperatures varying from 120 to 220° C.

15. PROCESS, according to claim 14, characterized by the fact that the washing uses small volumes of water (20 to 30% of the total reaction mass).

16. PROCESS, according to claim 9, characterized by the fact that the quantity of alkaline metal used in the preparation of the alcoxide varies from 0.03 to 3.0% of the total reaction mass.

17. PROCESS, according to claim 9, characterized by the fact that the preparation of the alcoxide and the transesterification are conducted in an inert atmosphere (nitrogen or argon) or under reduced pressure (>600 mmHg).

* * * * *